United States Patent [19]
Heldreth et al.

[11] Patent Number: 5,405,396
[45] Date of Patent: Apr. 11, 1995

[54] TIBIAL PROSTHESIS

[75] Inventors: Mark A. Heldreth, Mentone; Dale E. Hileman, Akron; Jay T. Vansickle, Leesburg, all of Ind.

[73] Assignee: Zimmer, Inc., Warsaw, Ind.

[21] Appl. No.: 85,714

[22] Filed: Jul. 1, 1993

[51] Int. Cl.6 .............................................. A61F 2/38
[52] U.S. Cl. .................................................... 623/20
[58] Field of Search .......................................... 623/20

[56] References Cited

U.S. PATENT DOCUMENTS

| | | | |
|---|---|---|---|
| 4,277,129 | 3/1981 | Volz | 3/1.911 |
| 4,711,639 | 12/1987 | Grundei | 623/20 |
| 4,714,474 | 12/1987 | Brooks, Jr. et al. | 623/20 |
| 4,936,853 | 6/1990 | Fabian et al. | 623/20 |
| 4,938,769 | 7/1990 | Shaw | 623/20 |
| 4,944,757 | 7/1990 | Martinez et al. | 623/20 |
| 4,950,298 | 8/1990 | Gustilo et al. | 623/20 |
| 4,963,152 | 10/1990 | Hofmann et al. | 623/18 |
| 5,007,933 | 4/1991 | Sidebotham et al. | 623/20 |
| 5,061,271 | 10/1991 | Van Zile | 623/20 |
| 5,071,438 | 12/1991 | Jones et al. | 623/20 |
| 5,080,675 | 1/1992 | Lawes et al. | 623/20 |
| 5,147,405 | 9/1992 | Van Zibe et al. | 623/20 |
| 5,192,328 | 3/1993 | Winters | 623/20 |

FOREIGN PATENT DOCUMENTS

| | | | |
|---|---|---|---|
| 2223950 | 4/1990 | United Kingdom | 623/20 |

OTHER PUBLICATIONS

Brochure—Hybrid Fixation Modular Tibial Prosthesis—Shaw–Aspen Publishers—1991.
Brochure (p. 5)—Assembly/Dissembly of the Modular Components—Howmedica—1991.
Brochure (p. 6)—Total Knee System, Superstabilizer—Howmedica—1991.

*Primary Examiner*—Randy C. Shay
*Attorney, Agent, or Firm*—Cary R. Reeves

[57] ABSTRACT

A modular tibial prosthesis contains a dovetail mechanism (4, 5 & 14) and a posterior tongue (15) and groove (8) arrangement. The dovetail mechanism cooperates with a reinforcing component (22) to allow alternate use of a spined component (20) with the same base plate (1).

7 Claims, 3 Drawing Sheets

TIBIAL PROSTHESIS

BACKGROUND OF THE INVENTION

This invention relates to a prosthetic device for replacing the proximal tibial surface of a knee Joint. More particularly it relates to a means for attaching the components of a modular tibial prostheses to one another.

Modular tibial prostheses having a base plate and a separate articular surface component require a reliable means for attaching the articular surface component to the base plate. Ideally, the attachment means will provide easy assembly and prevent both sliding and separation between the plate and articular surface component. It is important that while achieving secure fixation the attachment means does not incorporate features that unnecessarily weaken the plate or articular surface component. These goals are particularly difficult to achieve in constrained knee designs which can transmit significant tilting loads to the articular surface component through a spine.

SUMMARY OF THE INVENTION

The present invention addresses these requirements by providing in a modular tibial prosthesis including a base plate and an articular component an interlocking two-segment dovetail mechanism. The plate has an upwardly extending rail around its periphery which merges with an upwardly extending two-segment dovetail. This continuous rail strengthens the base plate by eliminating notches along the plate periphery. This configuration is accommodated by the two-segment configuration which allows a continuous rail while maintaining dovetail engagement posteriorly. The two-segment dovetail also minimizes the dimensions of the anterior dovetail segment to reduce the requisite dovetail groove in the articular component thereby yielding a stronger articular component. The dovetail segments incorporate compound angles which engage a two-segment, compound angle, dovetail groove in the underside of the articular component to wedge the articular component against the proximal surface and anterior rail of the tibial plate. This wedging action resists sliding and separation between the tibial components.

In a preferred embodiment, the dovetail mechanism cooperates with a posterior tongue and groove arrangement to further resist separation of the tibial components.

The two-segment dovetail also allows the alternative use of an articular component having a reinforced spine on the same base plate design. A rigid reinforcing post extends upwardly into the spine to strengthen the spine and resist forces placed on the spine that would otherwise tend to separate the articular component and the base plate. The reinforcing post has a base portion that can be recessed into the articular component. The base portion contains a slot which avoids engagement between the rigid base portion and the anterior dovetail segment on the plate. However, the posterior dovetail segments of the articular surface and the plate still engage one another. The base portion also contains a through hole coaxial with a hole through the articular component and a hole in the base plate to accommodate a bolt for securely joining the components.

Figure 10:
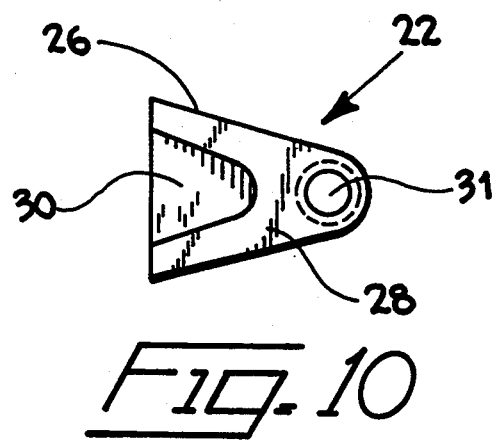
FIG. 10 is a bottom view of a reinforcing component.

2FIG. 11 is a side view of the component of FIG. 10.

Figure 12:
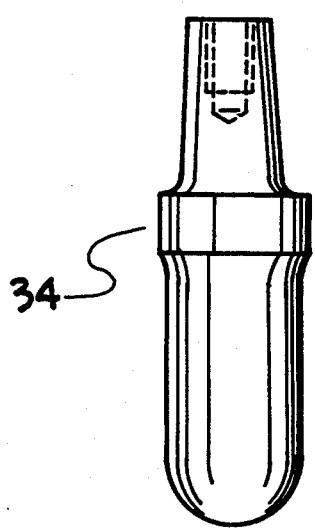

FIG. 12 is a side view of a stem extension.

DETAILED DESCRIPTION OF THE INVENTION

Figure 1:
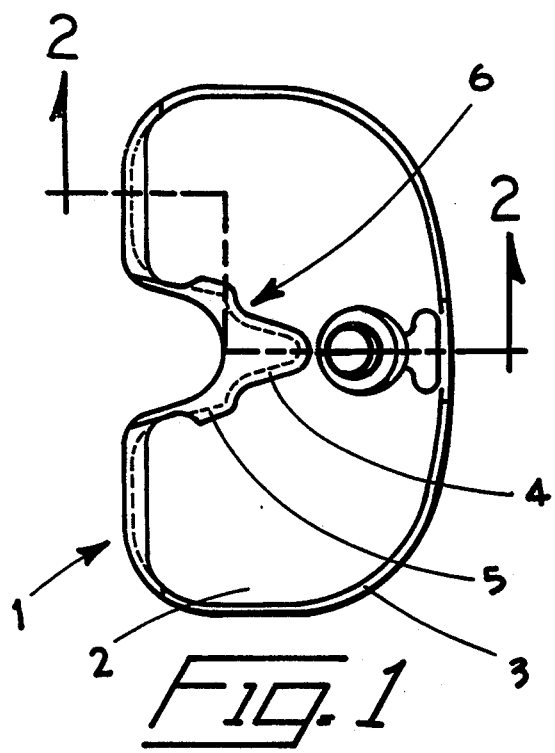
FIG. 1 is a top view of a tibial base plate.
Figure 2:
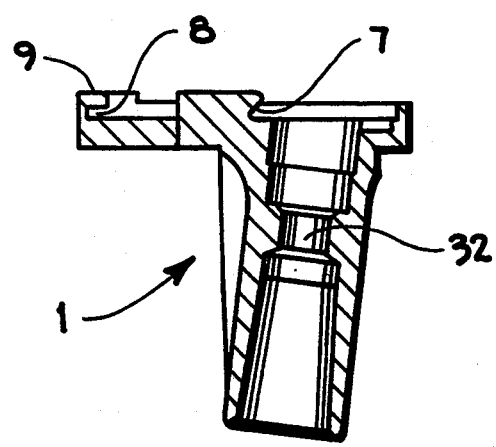
FIG. 2 is a section view of the tibial base plate of FIG. 1 cut along section line 2—2.

Referring to FIGS. 1 and 2, a tibial base plate 1 has a top surface 2 and an upwardly extending rail 3 around the periphery of the top surface 2. Also extending upwardly from the plate 1 top surface 2 is a two-segment dovetail comprising first 4 and second 5 segments. The rail 3 merges with the second segment 5 to eliminate notches in the posterior region of the plate 1 that could weaken the plate 1. The first segment 4 includes converging sides defining a lead-in angle. The first segment has a dovetail axis to which the converging sides converge to form the lead-in angle. The lead-in angle can vary from 1 to 179 degrees but is preferably about 32 degrees. The second segment 5 also includes converging sides converging to the same dovetail axis as the first segment and defining a lead-in angle. However, the second segment 5 sides are offset outwardly with respect to the first segment 4 sides and are therefore not co-linear with the first segment 4 sides. The first and second dovetail segments blend at a shoulder 6 to form a continuous, two-segment dovetail. Preferably the lead-in angle of the second segment 5 is the same as the lead-in angle of the first segment 4. The two-segment dovetail allows the continuous rail while maintaining dovetail engagement posteriorly, due to the offset of the second segment 5. It simultaneously minimizes the dimensions of the first, anterior, dovetail segment 4 to reduce the requisite dovetail groove in the articular component. This results in a stronger articular component with improved resistance to material cold flow. The two-segment dovetail has a dovetail angle 7 which can vary from 1 to 89 degrees but preferably is about 45 degrees. In the preferred embodiment the dovetail angle 7 is the same for both the first 4 and second 5 segments. The preferred embodiment also contains a posterior groove 8, formed as an undercut in a widened portion 9 of the posterior part of the rail 3. The base plate 1 is preferably formed made of metal to provide a strong and rigid support for the articular surface component.

Figure 4:
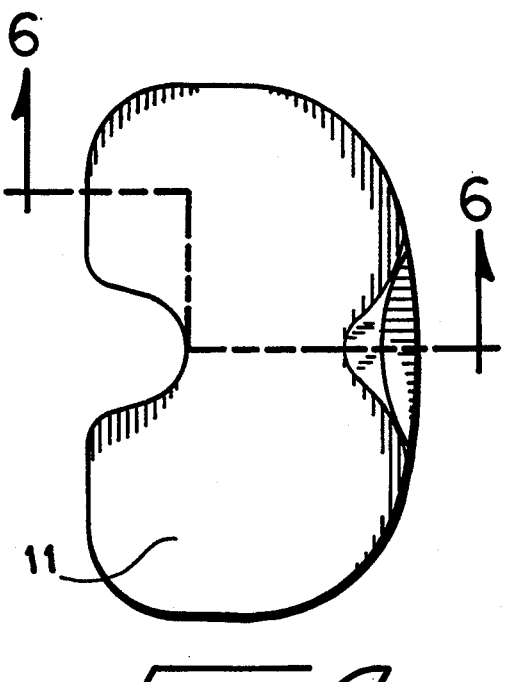
FIG. 4 is a top view of the component of FIG. 3.
Figure 5:
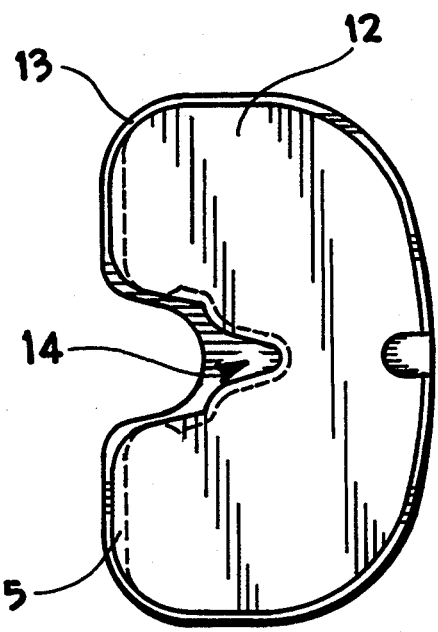
FIG. 5 is a bottom view of the component of FIG. 4.
Figure 3:
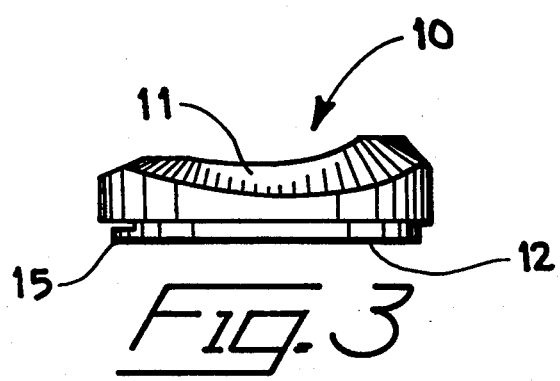
FIG. 3 is a side view of an articular surface component.

FIGS. 3–5 depict an articular surface component 10 which attaches to the top surface 2 of the tibial base plate 1. The articular component has an upper surface 11 for articular engagement with a femoral component and a lower surface 12 for matingly engaging the top surface 2 of the plate 1. A stepped edge 13 around the periphery of the articular component 10 is adapted to engage the rail 3 to resist outward migration of the component when it is compressively loaded. A two-segment dovetail slot 14 corresponding to the two-segment dovetail is formed in the lower surface 12. The preferred embodiment includes a posterior tongue 15 adapted to engage the posterior groove 8. The articular surface component 10 is preferably made from a polymer such as polyethylene which has natural lubricity to aid in articulation with a femoral component and which is elastically deformable to allow the dovetail interface described below.

Figure 6:
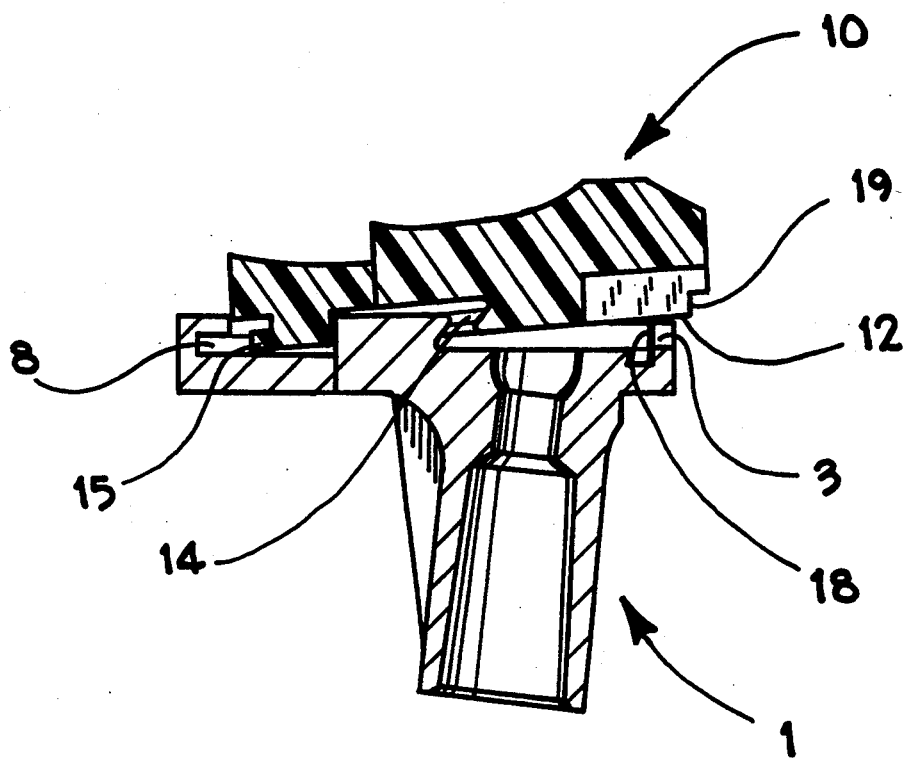
FIG. 6 is a section view of the articular component being placed on the tibial base plate, the components being cut along section lines 2—2 and 6—6.
Figure 7:
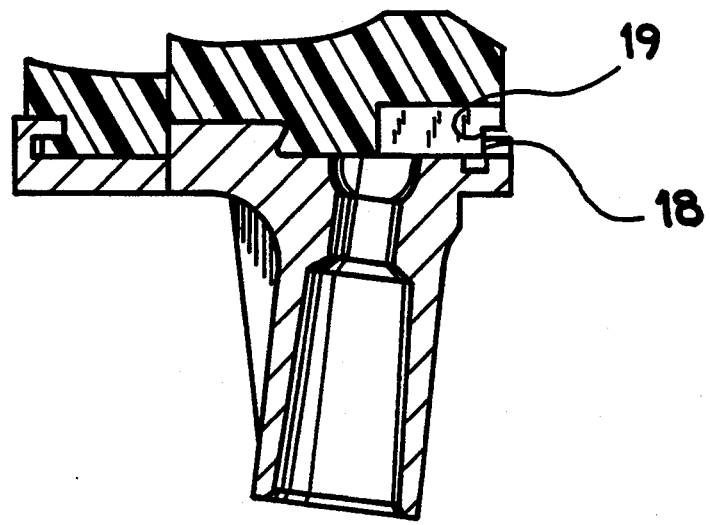
FIG. 7 is a section view similar to FIG. 6 showing the components fully assembled.
Figure 8:
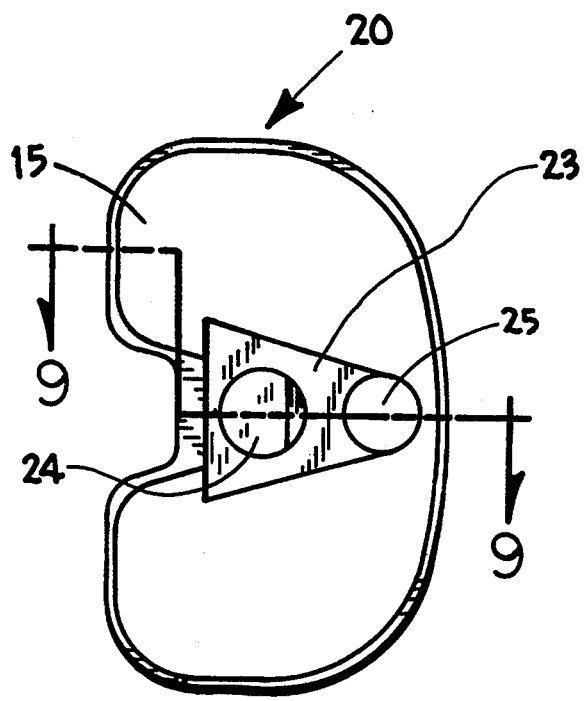
FIG. 8 is a bottom view of an alternative embodiment of the articular surface component.
Figure 9:
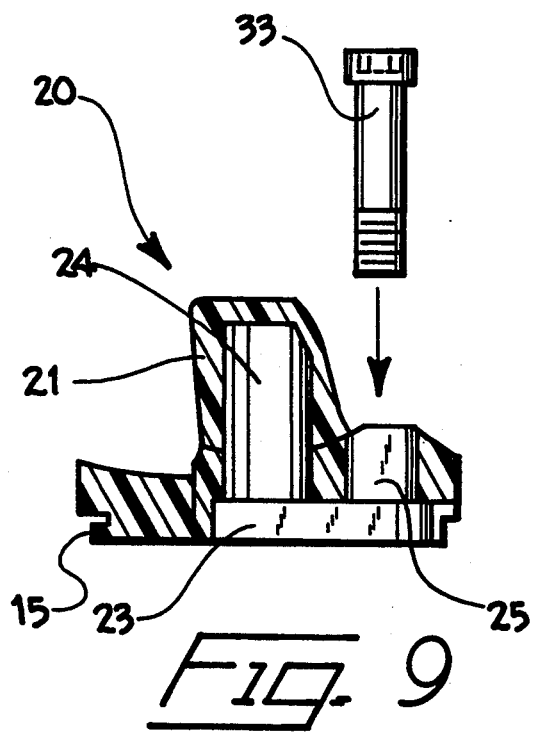
FIG. 9 is a section view of the component of FIG. 8 cut along section line 9—9, the figure also showing a screw.
Figure 11:
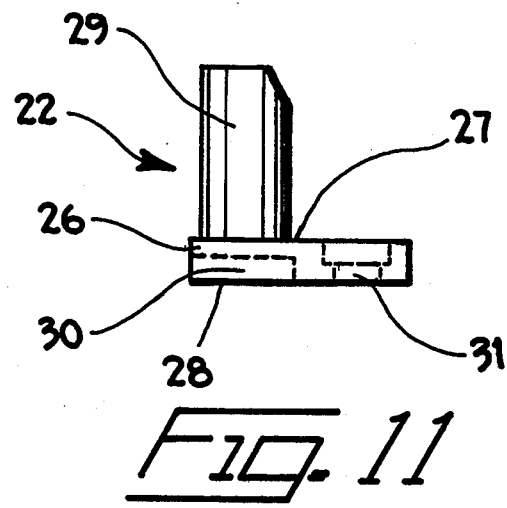

In use the articular surface component 10 is positioned with its lower surface 12 in contact with the top of the rail 3 and with the dovetail segments 4 and 5 in alignment with the two-segment dovetail slot 14 as shown in FIG. 6. With a downward and rearward force, the articular component 10 is urged into engagement with the plate 1. The two-segment dovetail slot engages the first segment 4 first and then the second segment 5 and the tongue 15 engages the groove 8. As the dovetail engages the dovetail slot, the slot elastically deforms creating reactive forces tending to move the articular component forward, toward the front portion of the rail 18, and downward, toward the top 2 of the plate 1. These forces occur due to the lead-in angle and dovetail angle 7 respectively. These reactive forces are advantageously distributed over both dovetail segments 4 and 5. As the front edge 19 of the articular component 10 clears the rail 3, the articular component 10 moves to seat against the plate 1. When the user removes the downward and rearward force, the reactive forces from the elastic deformation of the articular component 10 cause the articular component's lower surface 12 and front edge 19 to press firmly against the plate's top surface 2 and the front portion 18 of the rail 3, respectively, as shown in FIG. 7.

In an alternative embodiment, shown in FIGS. 8–12, a spined articular component 20 includes a spine 21 for constraining the motion of a femoral component. The spined component is strengthened and further secured by a reinforcing component 22. The reinforcing component is preferably made from a metal to provide sufficient strength and rigidity. The spined component contains a recessed area 23 and a post hole 24 and a bolt hole 25. The reinforcing component 22 comprises a base portion 26 having a top 27 and a bottom 28. A post 29 extends from the top 27 of the base portion 26. The bottom 28 contains a clearance slot 30. A bolt hole 31 extends through the base portion 26. The reinforcing component 22 fits within the spined component 20 with the post 29 extending into the post hole 24 and the base portion 26 within the recess 23. The bolt hole 31 in the base portion 26 aligns with the bolt hole 25 in the spined component 20.

In use, the reinforcing component 22 is placed within the spined component 20 and then the spined component 20 is placed on the tibial base plate 1 as described for the previous embodiment. However, the clearance slot 30 of the rigid base portion 26 fits over the first segment 4 of the dovetail and does not engage it. The second segment 5 does engage the dovetail slot 14 and the tongue 15 engages the groove 8. When the spined component 20 is seated on the base plate 1, the bolt holes 25 and 31 align with a bolt hole 32 in the base plate 1. A bolt 33 is placed through the bolt holes 25, 31 and 32 to engage a nut, or preferably a threaded stem extension 34, as shown in FIG. 12. The bolt. 33 passes completely through the bolt hole 25 in the spined component 20 and abuts the base portion 26 of the reinforcing component 22. When the bolt 33 is tightened, the base portion 26 of the reinforcing component 22 is pressed tightly against the top 2 of the plate. Because of the close engagement of the post 29 and the walls of the post hole 24, forces that would tend to displace the spine 21 are transmitted to the post 29 and therefore to the plate 1. The reinforcing component 22 in conjunction with the engagement of the second dovetail segment 5 with the dovetail slot 14 and the engagement of the tongue 15 and groove 8 provides secure fixation of the spined component 20 to the plate 1. This is because in order for the spined component 20 to disengage from the base plate 1, it must be displaced in a tilting or sliding manner which is prevented by the reinforcing component 22 and bolt 33.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. An implant for the human knee comprising a tibial base plate having:
    a generally planar top surface;
    a first dovetail segment extending upwardly from the top surface and forming a dovetail angle with the top surface, the first dovetail segment having an axis and sides converging to the axis, the converging sides forming a lead-in angle; and
    a second dovetail segment extending upwardly from the top surface and forming a dovetail angle with the top surface, the second dovetail segment having sides converging to the axis, the converging sides forming a lead-in angle, the converging sides of the second segment being offset with respect to the converging sides of the first segment such that the converging sides of the first segment are not collinear with the converging sides of the second segment.

2. The implant of claim 1 further comprising a rail extending above the top surface and extending substantially all the way around the top surface.

3. The implant of claim 2 wherein a portion of the rail is undercut to form a tongue receiving groove.

4. An implant for the human knee comprising a tibial base plate having:
    a generally planar top surface;
    a first dovetail segment extending upwardly from the top surface and having converging sides;
    a second dovetail segment extending upwardly from the top surface and having converging sides, the converging sides of the second segment being offset with respect to the converging sides of the first segment such that the converging sides of the first segment are not collinear with the converging sides of the second segment;
    a rail extending above the top surface and extending substantially all the way around the top surface, a portion of the rail being undercut to form a tongue receiving groove; and a tibial articular surface having:
        an upper surface for articulation with a femoral implant;
        a lower surface in engagement with the tibial base plate, the lower surface having an outer edge fitting within the rail, the lower surface further containing a dovetail groove receiving the first and second dovetail segments; and a tongue formed in a portion of the outer edge, the tongue fitting within the tongue receiving groove.

5. The implant of claim 4 further comprising:

a spine extending upwardly from the upper surface, the spine containing a post hole, the post hole opening onto the lower surface;

a reinforcing component having a base portion with a top and a bottom, the base portion having a post extending upwardly from its top, the post fitting within the post hole, and a clearance slot formed in the bottom which fits over the first dovetail segment without engaging the dovetail angle.

6. A prosthetic implant for the knee comprising:

a tibial base plate having a generally planar top surface;

a tibial articular surface component having an upper surface and a lower surface, the lower surface engaging the planar top surface;

a spine extending upwardly from the upper surface, the spine containing a post hole, the post hole opening onto the lower surface;

a reinforcing component having a base portion with a top and a bottom, the base portion having a post extending upwardly from its top, the post fitting within the post hole; and a bolt, wherein the articular surface component contains a hole extending completely through it from the upper surface to the lower surface and the reinforcing component contains a hole extending through it from its top to its bottom and the base plate contains a hole in its top surface such that when the post is placed in the post hole and the articular surface component is placed on the base plate the bolt can be placed through the holes in all three components simultaneously, the bolt passing through the hole in the articular component and coming to bear on the reinforcing component in order to press the reinforcing component tightly against the base plate when the bolt is tightened.

7. A prosthetic implant for the knee comprising:

a tibial base plate having a generally planar top surface;

a tibial articular surface component having an upper surface and a lower surface, the lower surface engaging the planar top surface;

a spine extending upwardly from the upper surface, the spine containing a post hole, the post hole opening onto the lower surface;

a reinforcing component having a base portion with a top and a bottom, the base portion having a post extending upwardly from its top, the post fitting within the post hole; and a dovetail extending upwardly from the top surface of the base plate, wherein the base portion of the reinforcing component contains a clearance slot which fits over a portion of the dovetail without engaging the dovetail when the post is placed in the post hole and the articular surface component is placed on the base plate.

* * * * *